(12) United States Patent
Wang et al.

(10) Patent No.: US 12,175,666 B2
(45) Date of Patent: Dec. 24, 2024

(54) SYSTEMS AND METHODS FOR CLASSIFYING BIOMEDICAL IMAGE DATA USING A GRAPH NEURAL NETWORK

(71) Applicant: PathAI, Inc., Boston, MA (US)

(72) Inventors: Jason Ku Wang, Los Angeles, CA (US); Maryam Pouryahya, Bethesda, MD (US); Kenneth K. Leidal, Melrose, MA (US); Oscar M. Carrasco-Zevallos, Somerville, MA (US); Ilan Wapinski, Brookline, MA (US); Amaro Taylor-Weiner, Brooklyn, NY (US)

(73) Assignee: PathAI, Inc., Boston, MA (US)

( * ) Notice: Subject to any disclaimer, the term of this patent is extended or adjusted under 35 U.S.C. 154(b) by 305 days.

(21) Appl. No.: 17/590,642

(22) Filed: Feb. 1, 2022

(65) Prior Publication Data

US 2022/0245802 A1 Aug. 4, 2022

Related U.S. Application Data

(60) Provisional application No. 63/144,318, filed on Feb. 1, 2021.

(51) Int. Cl.
*G06T 7/00* (2017.01)
*G06V 10/44* (2022.01)
(Continued)

(52) U.S. Cl.
CPC .......... *G06T 7/0012* (2013.01); *G06V 10/454* (2022.01); *G06V 10/457* (2022.01);
(Continued)

(58) Field of Classification Search
CPC .............. G06T 7/0012; G06T 7/00; G06T 2207/20081; G06T 2207/20084;
(Continued)

(56) References Cited

U.S. PATENT DOCUMENTS

| 10,650,520 B1 | 5/2020 | Beck et al. |
| 2015/0110381 A1 | 4/2015 | Parvin et al. |

(Continued)

FOREIGN PATENT DOCUMENTS

| WO | WO-2020150258 A1 | 7/2020 |
| WO | WO-2022038527 A1 | 2/2022 |

OTHER PUBLICATIONS

Diehl, "Edge Contraction Pooling for Graph Neural Networks", https://arxiv.org/pdf/1905.10990, May 27, 2019 (9 pages).
(Continued)

*Primary Examiner* — Tuan H Nguyen
(74) *Attorney, Agent, or Firm* — Wilmer Cutler Pickering Hale and Dorr LLP (57) ABSTRACT

Techniques for classifying biomedical image data using a graph neural network are disclosed. In one particular embodiment, the techniques may be realized as a method for classifying biomedical image data comprising generating an annotated representation of biomedical image data; identifying a plurality of pixel clusters based on the biomedical image data; constructing a graph based on the plurality of pixel clusters; determining at least one biomedical feature for at least one node of the graph based on the annotated representation of the biomedical image data; and processing a graph neural network to classify the biomedical image data based on the at least one biomedical feature.

27 Claims, 3 Drawing Sheets

(51) Int. Cl.
G06V 10/762 (2022.01)
G06V 10/82 (2022.01)
G16H 30/20 (2018.01)
G16H 50/30 (2018.01)

(52) U.S. Cl.
CPC .......... *G06V 10/7635* (2022.01); *G06V 10/82* (2022.01); *G16H 30/20* (2018.01); *G16H 50/30* (2018.01); *G06T 2207/20081* (2013.01); *G06T 2207/20084* (2013.01); *G06T 2207/30056* (2013.01)

(58) Field of Classification Search
CPC .......... G06T 2207/30056; G06V 10/82; G06V 10/454; G06V 10/457; G06V 10/7635; G06V 10/44; G06V 10/762; G16H 30/20
See application file for complete search history.

(56) References Cited

U.S. PATENT DOCUMENTS

| | | | |
|---|---|---|---|
| 2016/0110584 A1* | 4/2016 | Remiszewski | G06V 20/69 382/133 |
| 2020/0150258 A1 | 5/2020 | Itkin | |
| 2020/0258223 A1* | 8/2020 | Yip | G06V 10/82 |
| 2020/0342597 A1 | 10/2020 | Chukka et al. | |

OTHER PUBLICATIONS

International Search Report and Written Opinion issued by the U.S. Patent and Trademark Office in International Application No. PCT/US22/14778, dated May 12, 2022 (11 pages).

Krizhevsky, et al., "ImageNet Classification with Deep Convolutional Neural Networks", original version published in *Proceedings of the 25th International Conference on Neural Information Processing Systems*, Lake Tahoe, NV, pp. 1097-1105, Dec. 2012, Communications of the ACM, 60(6):84-90, Jun. 2017 (7 pages).

Lee, et al., "Self-Attention Graph Pooling", Proceedings of the 36th International Conference on Machine Learning, Long Beach, California, PMLR97, https://arXiv:1904.08082v4, Jun. 13, 2019 (10 pages).

Morris, et al., "Weisfeiler and Leman Go Neural: Higher-Order Graph Neural Networks", *Association for the Advancement of Artificial Intelligence, Thirty-Third AAAI Conference on Artificial Intelligence (AAAI-19)*, 33(01), 4602-4609, 2019 (8 pages).

Szegedy, et al., "Going Deeper with convolutions", 2015 IEEE Conf. on Computer Vision and Pattern Recognition, https://arXiv:1409.4842v1, Sep. 17, 2014 (12 pages).

Wang, et al., "Face Search at Scale: 80 Million Gallery", MSU Technical Report MSU-CSE-15-11, https://arXiv:1507.07242v2, Jul. 24, 2015 (15 pages).

Zhang, et al., "BIRCH: An Efficient Data Clustering Method for Very Large Databases", Proc. 1996 ACM SIGMOD Intl. Conf. on Management of Data, Montreal, Canada, 103-114 (1996).

Adnan, et al., "Representation Learning of Histopathology Images using Graph Neural Networks", IEEE/CVF Conference on Computer Vision and Pattern Recognition Workshops (CVPRW), pp. 4254-4261, 2020 (8 pages).

European Extended Search Report issued in European Application No. EP22746881.6, dated Oct. 24, 2024 (9 pages).

Levy, et al., "A large-scale internal validation study of unsupervised virtual trichrome staining technologies on nonalcoholic steatohepatitis liver biopsies", Modern Pathology, 34:808-822, 2021, published online Dec. 9, 2020 (15 pages).

* cited by examiner

SYSTEMS AND METHODS FOR CLASSIFYING BIOMEDICAL IMAGE DATA USING A GRAPH NEURAL NETWORK

RELATED APPLICATIONS

This application claims priority to U.S. Provisional Application No. 63/144,318, entitled "Systems and Methods for Classifying Biomedical Image Data Using a Graph Neural Network," filed Feb. 1, 2021, which is incorporated by reference herein in its entirety.

FIELD OF THE DISCLOSURE

The present disclosure generally relates to classification of biomedical image data and, more particularly, to techniques for automatically classifying biomedical image data using a graph neural network.

BACKGROUND OF THE DISCLOSURE

The classification of biomedical images is performed in widespread applications, such as the study and treatment of diseases. An example of a disease that is often studied using biomedical image data is nonalcoholic fatty liver disease (NAFLD). The global prevalence of NAFLD is rising rapidly and there is an urgent and unmet medical need for new therapies to address this growing medical problem. NAFLD represents a continuum of disease of varying severity. The milder forms consist of simple steatosis, while the progressive form, nonalcoholic steatohepatitis (NASH), can progress to cirrhosis and end-stage liver disease. NASH-related cirrhosis is now the fastest growing indication for liver transplantation in the United States.

Clinical trials in NASH are carried out by performing detailed pathological reviews of liver biopsies for both study inclusion and assessment of treatment response. However, due to inter-pathologist and intra-pathologist variability in grading and staging, and the fact that manual pathology review may not be quantitative, current practices are impacted by inconsistency and insensitivity.

Thus, it may be understood that there may be a need for improved techniques for classifying biomedical images.

SUMMARY OF THE DISCLOSURE

Techniques for classifying biomedical image data using a graph neural network are disclosed. In one particular embodiment, the techniques may be realized as a method for classifying biomedical image data, the method comprising generating, by at least one computer processor, an annotated representation of biomedical image data; identifying, by the at least one computer processor, a plurality of pixel clusters based on the biomedical image data; constructing, by the at least one computer processor, a graph based on the plurality of pixel clusters; determining, by the at least one computer processor, at least one biomedical feature for at least one node of the graph based on the annotated representation of the biomedical image data; and processing, by the at least one computer processor, a graph neural network to classify the biomedical image data based on the at least one biomedical feature.

In accordance with other aspects of this particular embodiment, classifying the biomedical image data includes predicting a severity of a disease condition.

In accordance with other aspects of this particular embodiment, the biomedical image data comprises a hematoxylin and eosin (H&E) stained whole slide image, and classifying the biomedical image data includes predicting a non-alcoholic fatty liver disease activity score (NAS) based on the H&E stained whole slide image.

In accordance with other aspects of this particular embodiment, the biomedical image data comprises a trichrome-stained whole slide image, and wherein classifying the biomedical image data includes predicting a Clinical Research Network (CRN) score based on the trichrome-stained whole slide image.

In accordance with other aspects of this particular embodiment, the graph neural network comprises at least one graph convolution module and at least one graph pooling module. In some embodiments, the at least one graph pooling module may use edge pooling or self-attention pooling.

In accordance with other aspects of this particular embodiment, the method may further include training the graph neural network using a mixed effects model, wherein the training comprises learning one or more bias parameters associated with each individual that assigned a label to the labeled training data; and adjusting a prediction of the graph neural network based on the one or more bias parameters when training using the labeled training data labeled by the corresponding individual. In some embodiments, the training may further comprise testing the graph neural network model without adjusting the prediction based on the one or more bias parameters associated with each individual.

In accordance with other aspects of this particular embodiment, the at least one biomedical feature comprises an aggregate metric based on at least one second biomedical feature identified in the annotated representation of the biomedical image data. For example, the aggregate metric may include at least one of a mean, a standard deviation, a skewness, a kurtosis, or an entropy of the at least one second biomedical feature associated with each pixel cluster among the plurality of pixel clusters.

In accordance with other aspects of this particular embodiment, the method may further include determining, by the at least one computer processor, at least one spatial feature for the at least one node of the graph, wherein the at least one spatial feature includes at least one of a mean, a standard deviation, or a skewness of spatial coordinates associated with each pixel cluster among the plurality of pixel clusters.

In accordance with other aspects of this particular embodiment, constructing the graph comprises determining spatial coordinates associated with each of the plurality of pixel clusters.

In accordance with other aspects of this particular embodiment, constructing the graph comprises determining providing one or more directed edges between at least one pair of nodes, where each of the one or more directed edges includes a source node and a target node. In some embodiments, the one or more directed edges are provided in response to determining that the at least one pair of nodes are within a threshold distance. For example, the threshold distance may be based on at least one size dimension associated with the biomedical image data.

In accordance with other aspects of this particular embodiment, constructing the graph comprises providing a self-loop for at least one node of the graph.

In accordance with other aspects of this particular embodiment, constructing the graph comprises determining that the graph includes at least one pair of disconnected components, and adding at least one edge to connect the at least one pair of disconnected components.

In accordance with other aspects of this particular embodiment, identifying the plurality of pixel clusters comprises randomly sampling a plurality of pixels from the biomedical image data; processing the randomly sampled plurality of pixels into the plurality of pixel clusters; and assigning a remaining plurality of pixels from the biomedical image data to a corresponding pixel cluster among the plurality of pixel clusters based on a nearest neighbor among the randomly sampled plurality of pixels. In some embodiments, processing the randomly sampled plurality of pixels into the plurality of pixel clusters is based on the BIRCH clustering algorithm.

In accordance with other aspects of this particular embodiment, the annotated representation of the biomedical image data includes annotations that identify at least one of a presence of tissue at a pixel location, a type of tissue at the pixel location, or a presence of a biomedical condition at the pixel location.

In accordance with other aspects of this particular embodiment, generating the annotated representation includes processing the biomedical image data using one or more convolutional neural network models. In some embodiments, the annotated representation is based on logit values generated by the one or more convolutional neural network models.

In another particular embodiment, the techniques may be realized as a system for classifying biomedical image data comprising at least one computer processor communicatively coupled to and configured to operate in the biomedical image classification system, wherein the at least one computer processor is further configured to perform the steps in the above-described method.

In another particular embodiment, the techniques may be realized as an article of manufacture for classifying biomedical image data with a biomedical image classification system comprising a non-transitory processor readable medium and instructions stored on the medium, wherein the instructions are configured to be readable from the medium by at least one computer processor communicatively coupled to and configured to operate in the biomedical image classification system and thereby cause the at least one computer processor to operate so as to perform the steps in the above-described method.

The present disclosure will now be described in more detail with reference to particular embodiments thereof as shown in the accompanying drawings. While the present disclosure is described below with reference to particular embodiments, it should be understood that the present disclosure is not limited thereto. Those of ordinary skill in the art having access to the teachings herein will recognize additional implementations, modifications, and embodiments, as well as other fields of use, which are within the scope of the present disclosure as described herein, and with respect to which the present disclosure may be of significant utility.

BRIEF DESCRIPTION OF THE DRAWINGS

To facilitate a fuller understanding of the present disclosure, reference is now made to the accompanying drawings, in which like elements are referenced with like numerals. These drawings should not be construed as limiting the present disclosure, but are intended to be illustrative only.

DETAILED DESCRIPTION

Whereas manual classification of biomedical images may be impacted by inconsistency and insensitivity, automated methods based on neural networks may provide various improvements. For example, automated classification techniques may standardize quantification of disease histology and thus increase sensitivity to monitor treatment efficacy and disease progression. Illustrative types of neural networks that may be applied to automated classification of biomedical images include convolutional neural networks (CNNs) and graph neural networks (GNNs).

GNNs are an emerging deep learning method that can capture the dependence of graphs via message passing between the nodes of a graph structure. While convolutional neural networks CNNs generate increasingly complex representations of an image by aggregating information across neighboring pixels in a uniform lattice, GNNs aggregate information across neighboring nodes encoding irregular patterns. GNNs are particularly well-suited for data types that can be modeled in a graph structure, such as cell clusters, chemical structures, and fibrosis clusters.

In some digital pathology applications, GNNs may be used to classify raw biomedical image data associated with whole slide images (WSIs). However, applying a GNN directly to biomedical image data relies on the GNN to learn a high dimensional feature representation corresponding, for example, to each pixel value in the image. Such an approach may be inefficient, using a large amount of training data and computational resources, and may reduce the accuracy of the classifications.

Accordingly, there is a desire for improved techniques for classifying biomedical images using GNNs that addresses these challenges.

Figure 1:
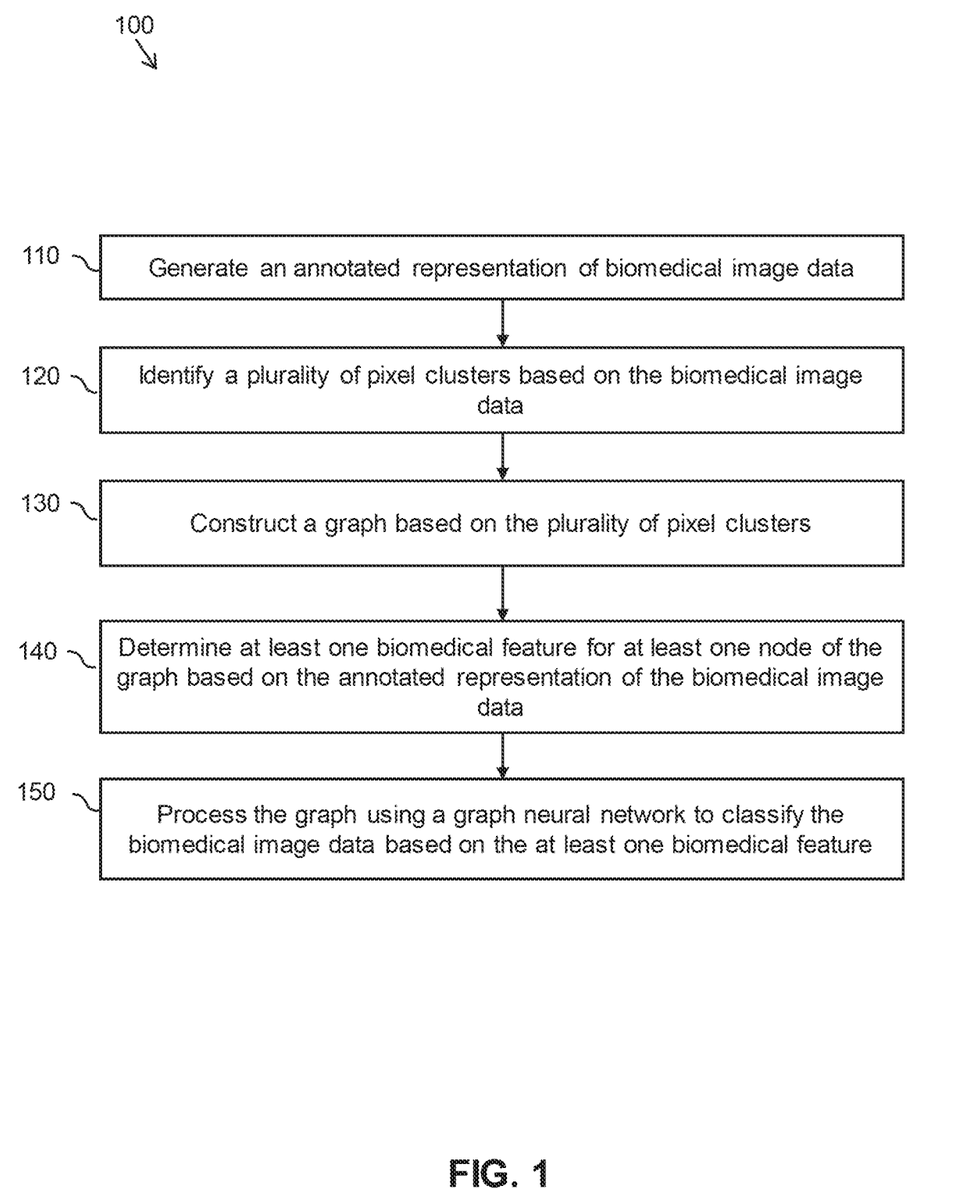
FIG. 1 shows a flow diagram of a method for classifying biomedical image data using a graph neural network according to some embodiments.

FIG. 1 shows a flow diagram of a method 100 for classifying biomedical image data using a graph neural network according to some embodiments. The use of an annotated representation in the classification of biomedical image data according to method 100 may result in a more data efficient, robust, and spatially resolved learning paradigm. Method 100 may be used in a variety of applications that perform classification of biomedical image data, such as digital pathology.

At method step 110, an annotated representation of biomedical image data is generated. The biomedical image data may correspond to image data received, for example, from a clinical setting, such as a biopsy. The received image data may include pixel values (e.g., intensity values). In the annotated representation, the pixel values are augmented or replaced with information that identifies one or more biomedical features of the biomedical image data at each pixel location. In some embodiments, the biomedical features may include features with a known relevance (e.g., a statistical relationship) to a clinical outcome, such as a disease diagnosis. For example, the biomedical features may include the presence or absence of tissue at or near a pixel location, the type of tissue (e.g., blood vessel, lumen, or other tissue), the presence of a biomedical condition (e.g., inflammation, fibrosis, steatosis, or the like), or a combination thereof. The annotated representation may include any suitable data structure that identifies the annotations and their locations with respect to the original image data.

In some embodiments, generating the annotated representation may include processing the received biomedical image data using one or more convolutional neural network models. For example, the convolutional neural networks may be trained to annotate biomedical image data using data from whole slide images (WSIs), e.g., stained WSIs collected during clinical trials. In some embodiments, the training data may include biomedical image data annotated by qualified individuals, e.g., physicians, pathologists, or others qualified to interpret the biomedical image data. The output of the convolutional neural network may include information that indicates the presence or absence of a given biomedical feature at a given pixel location, a discrete or continuous measure of strength associated with a given biomedical feature, or the like. In some embodiments, the output may include a measure of probability, such as a logit, that indicates the likelihood that a given biomedical feature is present at the pixel location. In some embodiments, the one or more convolutional neural networks may include multi-class models that each evaluate a plurality of biomedical features, single-class models that each evaluate a single biomedical feature, or a combination thereof. Illustrative examples of convolutional neural networks are described, for example, in Szegedy et al., "Going Deeper with Convolutions," 2015 *IEEE Conf. on Computer Vision and Pattern Recognition* (2015); Krizhevsky et al., "ImageNet Classification with Deep Convolutional Neural Networks," *Advances in Neural Image Processing Systems* 25, 1097-1105 (2012); and Wang et al., "Face Search at Scale: 80 Million Gallery," arXiv:1507.07242 (2015); each of which is incorporated by reference herein in its entirety.

Illustrative techniques for generating an annotated representation of biomedical image data consistent with method step 110 is discussed in further detail in U.S. Pat. No. 10,650,520, entitled "Systems and Methods for Training a Statistical Model to Predict Tissue Characteristics for a Pathology Image," filed Jun. 6, 2018, which is incorporated by reference herein in its entirety.

At method step 120, a plurality of pixel clusters based on the biomedical image data are identified. In some embodiments, each pixel cluster may correspond to a superpixel that includes a plurality of pixels of the annotated biomedical image data. Identifying pixel clusters may improve computational efficiency due to the smaller number of superpixels relative to the number of pixels in the original image. In some embodiments, identifying the plurality of pixel clusters may include randomly sampling pixels from the biomedical image data, processing the sampled pixels into clusters using a clustering algorithm, and assigning the remaining pixels from the image (including those that were not among the sampled pixels) to a cluster. In some embodiments, the remaining pixels may be assigned to the cluster of their nearest neighbor among the sampled pixels. An example of a clustering algorithm is described in further detail in Zhang, et al., "BIRCH: an efficient data clustering method for very large databases," *Proc.* 1997 *ACM SIGMOD Intl. Conf. on Management of Data*, 103-114 (1997), which is incorporated by reference herein in its entirety. In some embodiments, one or more pixels may be included or excluded from the pixel clusters based on the biomedical features associated with the pixels. For example, pixels that are identified as part of the image background or as having a tissue type that is not among the relevant types ("other" tissue) may be excluded.

At method step 130, a graph is constructed based on the plurality of pixel clusters. In some embodiments, each pixel cluster may correspond to a node of the graph. The spatial relationship among the nodes may be represented in a suitable manner, such as coordinates in Euclidean space. The coordinates for each node may correspond, to example, to the geometric center of each cluster. Constructing the graph may include providing directed edges between selected pairs of nodes, where each directed edge includes a source node and a target node. A bi-directional edge may include a pair of directed edges, one in each direction. Directed edges (including bi-directional edges) may be constructed between each node and one or more other nodes. For example, directed edges may be constructed by connecting each node to a predetermined number of nearest neighbor nodes, connecting each node to nodes that are within a predetermined radius of the given node, or the like. When the edge construction process results in one or more nodes that are not connected to other nodes, or separate graphs that each include a plurality of connected nodes but are not connected to each other, the disconnected nodes or graphs may be connected by a suitable technique. For example, edges may be iteratively added between the closest nodes of the disconnected graphs. In some embodiments, the graph may include self-loops, where each node is connected to itself by a directed edge.

At method step 140, at least one biomedical feature is determined for at least one node of the graph based on the annotated representation of the biomedical image data. For example, the graph nodes may be featurized to identify a plurality of features associated with each node. In some embodiments, the features for each node may include spatial features, topological features, biomedical features, or the like. The features may include aggregate metrics that are determined based on the features of the underlying pixels that make up each node. Illustrative examples of the spatial features of a given node may include the mean, standard deviation, and skewness of the spatial coordinates of the pixels in the node. Illustrative examples of the topological features for a given node may include the convexity, solidity, eccentricity, Euler characteristic, area, perimeter, and major/minor axis of the cluster area. For example, the cluster area may correspond to a box bounded by coordinate extremes of pixels that make up the node in each of four directions. Illustrative examples of the biomedical features for a given node may include the mean, standard deviation, skewness, kurtosis, and entropy of the biomedical features identified of the underlying pixels in the annotated representation of the biomedical image data.

At method step 150, the graph is processed using graph neural network to classify the biomedical image data. In some embodiments, the biomedical image data may be classified based on a clinical prediction associated with the biomedical image data, such as a prediction of the severity (e.g., a stage) of a disease condition. The classification may be identified using a known scoring or staging system. In this manner, during training, the classification of the graph neural network may be compared to classifications assigned by qualified individuals. Illustrative examples of graph neural networks are described, for example, in Morris et al., "Weisfeiler and Leman Go Neural: Higher-Order Graph Neural Networks," *Proc. AAAI Conf. on Artificial Intelligence,* 33(01), 4602-4609 (2019); Diehl, "Edge Contraction Pooling for Graph Neural Networks," arXiv:1905.10990 (2019); and Lee et al., "Self-Attention Graph Pooling," arXiv:1904.08082 (2019); each of which is incorporated by reference herein in its entirety. The graph neural network used at method step 150 may have any suitable architecture, such as the embodiments described in further detail below with reference to FIG. 2.

Because at least one biomedical feature is determined for at least one node of the graph at method step 140, the computational efficiency of method step 150 may be increased relative to approaches that do not use biomedical features as an input to the graph neural network. For example, the biomedical feature supplies biologically relevant information to the graph neural network, without which the graph neural network would be relied upon to learn the relevance of this feature during training. As a result, classification according to method 100 may use less training data and achieve higher prediction accuracy, and may achieve higher computational performance during training and prediction.

In some embodiments, the graph neural network may be trained by a process that reduces the impact of human bias in the training data. For example, a given individual responsible for classifying biomedical image data, such as a pathologist, may introduce systematic biases when classifying the images, e.g., by systematically over- or underestimating the severity of a condition. To account for this human bias, the labeled training data used to train the graph neural network (e.g., biomedical image data that has been previously classified by pathologists) may identify the individual that assigned each label. During training, when labeled training data associated with a particular individual is encountered, one or more bias parameters associated with that individual may be included in the graph neural network. For example, the one or more bias parameters may be added to (or otherwise used to adjust) the output of the unbiased graph neural network. In this manner, one or more bias parameters associated with each individual may be learned during the process of training of the graph neural network. These bias parameters may be discarded when testing and using the graph neural network to generate predictions on unlabeled data.

Figure 2:
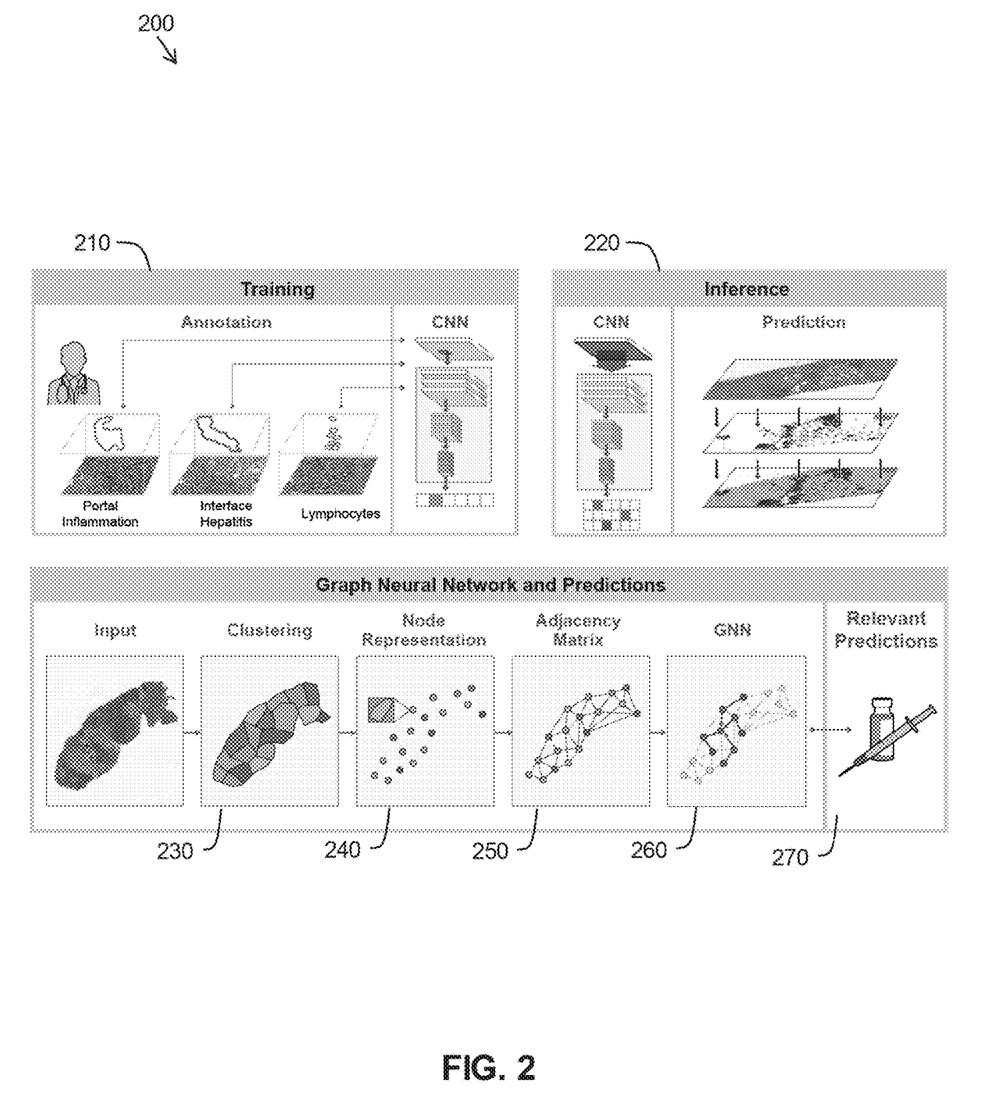
FIG. 2 shows a simplified diagram of a method for disease monitoring of NASH patients using a graph neural network according to some embodiments.

FIG. 2 shows a simplified diagram of a method 200 for disease monitoring of NASH patients using a graph neural network according to some embodiments. In some embodiments consistent with FIG. 1, method 200 may include classifying biomedical image data using a graph neural network consistent with method 100.

At method step 210, a convolutional neural network model is trained to annotate biomedical image data. For example, as shown in FIG. 2, hematoxylin and eosin (H&E) and trichrome-stained formalin-fixed paraffin-embedded (FFPE) WSIs collected in the course of clinical trials may be split into train, validation, and test sets. In order to compute histopathological image features for each slide, WSIs are annotated for relevant biological phenomena. For example, pathologists may label WSIs with polygonal region annotations based on relevant features. In illustrative embodiments, H&E-stained WSIs may be annotated to identify thirteen feature classes: microvesicular steatosis, steatosis, hepatocellular ballooning, hepatocellular swelling, normal hepatocytes, lumen, blood vessels, bile ducts, normal interface, interface hepatitis, portal inflammation, lobular inflammation, and background or other tissue. For trichrome-stained WSIs, five features classes may be annotated: blood vessel, lumen, bile duct, fibrosis, and background or other tissue.

Based on the annotated training sets, deep convolutional neural networks may be trained on H&E and trichrome-stained slides to output dense thirteen and five-class predictions, respectively. For example, the convolutional neural networks may have a 20× spatial resolution (spatial resolution dictated by stride). In some embodiments, to improve accuracy for feature extraction, the convolutional neural networks may be trained in an iterative process, with each updated model's predictions visualized to be reviewed by pathologists or other qualified individuals. For example, a model's predictions may be visualized by heatmap visualizations, in which feature categories are segmented into colored regions. This iterative training process may continue until systematic errors are below a predeterminate threshold.

At method step 220, a trained convolutional neural network is used to annotate unlabeled biomedical image data. The annotations may include predicted histopathological image features in the biomedical image data. For example, the trained convolutional neural network may generate thirteen-class or five-class logit predictions for each pixel in a WSI. These predictions may be pre-defined to be biological classes of known clinical relevance. By using these predictions as inputs to the graph neural network (see method step 260 below), rather than using a graph neural network to learn a feature set directly from the raw image data, the likelihood that the graph neural network considers spurious signals may be reduced. In addition, biological based feature representations may enable quantitative model interpretability and create a more data efficient learning paradigm by incorporating prior knowledge into model training.

At method step 230, clustering of the annotated biomedical image data is performed. In some embodiments, clustering may be performed by randomly sampling pixels from each WSI. These sampled pixels may be clustered into superpixels (e.g., using a computational efficient clustering method such as the Birch clustering method discussed above) based on spatial coordinates. The remaining pixels in the WSI may then be assigned to the cluster of their nearest neighbor from the clustered sampled pixels. In an illustrative embodiment, clustering may reduce the number of points by a factor of 100 or more. For example, a WSI may include hundreds of thousands of pixels, which may be reduced to several thousand (e.g., 5,000) superpixel clusters. In some embodiments, pixels where the maximum logit is associated with background or other tissue may be excluded from the clusters.

At method step 240, a graph is constructed based on the clustered biomedical image data. For example, pixel clusters may be used as nodes of a graph, locationally defined in Euclidean space by the geometric center of clustered pixels. Directed edges may be drawn between each node (source) and their nearest neighboring nodes (targets), with a predetermined maximum distance cutoff (e.g., 0.25×min(image height, image width)) to prevent edges being drawn between clusters from different tissue slices. Self-loops may be incorporated into the final graph structure. For WSIs where edge drawing results in one or more disconnected components, disconnected graphs may be connected iteratively by adding a bi-directional edge between the closest nodes between two separate graphs. Following graph construction at method step 240, each WSI may be represented by a single directed graph.

At method step 250, each node in the graph is featurized. In illustrative embodiments, each node (superpixel cluster) may be represented by three classes of features: spatial features, topological features, and logit-related features generated at method step 220. Spatial features may include the mean, standard deviation, and skewness of (x, y) spatial coordinates. Topological features may include the convexity, solidity, eccentricity, Euler characteristic, area, perimeter, and major/minor axis of the cluster area, defined as the box bounded by coordinate extremes of pixels in each of four directions. Logit-related features may include the mean, standard deviation, skewness, kurtosis, and entropy of logits for each of the classes, e.g., twelve and four features classes for H&E and trichrome-stained WSIs, respectively.

At method step 260, a graph neural network is applied to perform a graph-level ordinal classification of the biomedical image data. For example, components of the NAFLD Activity Score (NAS) (a composite ordinal scoring system comprising steatosis, lobular inflammation, and hepatocellular ballooning scores) may be determined based on H&E WSIs. A CRN score (a score based on the staging system developed by the Nonalcoholic Steatohepatitis Clinical Research Network (NASH CRN)) may be determined based on trichrome-stained WSIs. In some embodiments, the graph neural network may include graph convolution and graph pooling modules. The graph convolution module aggregates features from each nodes' local neighbors and generalizes the operation of convolution from grid data to graph data. An example of a graph convolution module is described, for example, in Morris et al., "Weisfeiler and Leman Go Neural: Higher-Order Graph Neural Networks," *Proc. AAAI Conf. on Artificial Intelligence*, 33(01), 4602-4609 (2019). Each hidden layer in the graph neural network transforms the input graph into another graph with updated node features. The graph pooling module enables the graph neural network to update the graph structure in addition to the node features. In some embodiments, the graph pooling module may use edge pooling, which learns to modify the graph structure by contracting the edges, as described, for example, in Diehl, "Edge Contraction Pooling for Graph Neural Networks," arXiv:1905.10990 (2019). In some embodiments, the graph pooling module may use self attention pooling, which masks the nodes based on the self-attention scores learned from the graph convolution and allows the pooling to consider both features and the graph structure, as described, for example, in Lee et al., "Self-Attention Graph Pooling," arXiv:1904.08082 (2019).

At method step 270, the graph neural network may be biased during training to reduce pathologist bias in the unbiased graph neural network. For example, there is historically moderate to weak pathologist concordance in patient NAS scoring. This lack of concordance is driven at least partially by different implicit labelling policies enacted by each pathologist despite sharing common guidelines. These differences lead to systematic biases where some pathologists may consistently overestimate the severity of patient disease while others underestimate. To account for this bias, the graph neural network is trained using a "mixed effects" model where each pathologist's policy is specified by a set of bias parameters which are learned during training and discarded at test time. To learn these biases, the biased graph neural network is trained on unique label-graph pairs (labeled training data), where the label is represented by a score as well as a variable which indicates which pathologist in the training set generated this score. The specified pathologist bias parameter is then selected and added it to the unbiased estimate of the disease state generated by the graph neural network. During training these biases are updated via back propagation on WSIs scored by the corresponding pathologists. When the graph neural network are deployed on unlabeled biomedical image data the classification is performed using the unbiased estimate of the graph neural network.

Tables 1 and 2, below, provide illustrative experimental results obtained by classifying biomedical images using graph neural networks in accordance with various embodiments described herein. Specifically, the results were obtained based on whole-slide images (WSI) of 639 H&E and 633 trichrome NASH liver biopsies from clinical trial participants (Cirius Therapeutics, NCT02784444). The WSIs were scored by 3 pathologists for NAFLD Activity (NAS 0-8) and its 3 components—inflammation (0-3), steatosis (0-3), and ballooning (0-2), and for fibrosis (0-4), respectively, and split into train, validation and test sets. A pathologist network annotated WSIs for tissue regions. Using the annotations, CNNs were trained to generate pixel-level predictions of 13 H&E and 5 trichrome classes (e.g., hepatocytes, bile duct etc.). WSIs were then converted into directed graphs via pixel-clustering (Birch method) and graph construction (treating each cluster as a node, directed edges were drawn between each node and its 5 nearest nodes). Each node was characterized by spatial and biological features (e.g., cluster size, bile duct pixels, etc.). GNNs were trained to grade biopsies for predict NAS and its 3 components (H&E), and fibrosis (trichrome). To account for inter-pathologist variability, a mixed-effects model was implemented to learn pathologist-specific biases during training (discarded during testing).

TABLE 1

| Prediction Task | Train Accuracy | Train Cohen's Kappa | Validation Accuracy | Validation Cohen's Kappa | Test Accuracy | Test Cohen's Kappa |
| --- | --- | --- | --- | --- | --- | --- |
| NAS Score (0-8) | 0.589 | 0.736 | 0.432 | 0.629 | 0.465 | 0.613 |
| Steatosis (0-3) | 0.850 | 0.846 | 0.700 | 0.783 | 0.770 | 0.758 |
| Lobular Inflammation (0-3) | 0.764 | 0.588 | 0.716 | 0.539 | 0.748 | 0.584 |
| Ballooning (0-2) | 0.793 | 0.741 | 0.684 | 0.603 | 0.709 | 0.614 |
| CRN Score (0-4) | 0.663 | 0.654 | 0.548 | 0.482 | 0.548 | 0.507 |

TABLE 2

| Prediction Task | Pathologist 1 | Pathologist 2 | Pathologist 3 |
| --- | --- | --- | --- |
| NAS | 0.11 | 0.36 | −0.38 |
| Ballooning Score | −0.56 | 0.59 | −0.18 |
| Steatosis Score | 0.75 | 0.45 | −0.95 |
| Inflammation Score | 0.0 | 0.025 | −0.014 |
| CRN Score | −0.48 | 1.05 | −0.77 |
| Mean Bias | −0.036 | 0.495 | −0.459 |

Figure 3:
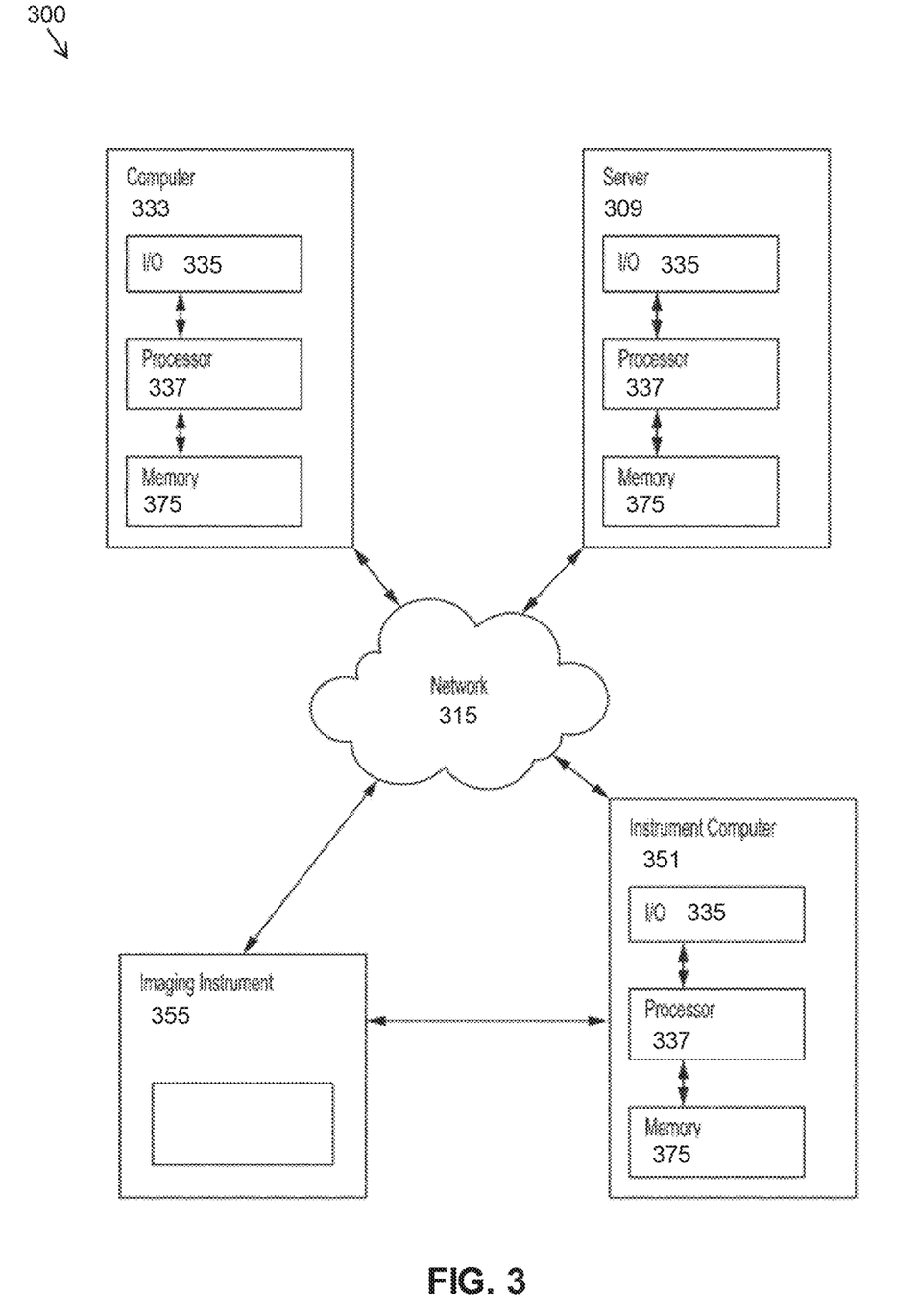
FIG. 3 shows a block diagram of a computer system on which various embodiments of the technology described herein may be practiced.

FIG. 3 shows a block diagram of a computer system on which various embodiments of the technology described herein may be practiced. The system 300 includes at least one computer 333. Optionally, the system 300 may further include one or more of a server computer 309 and an imaging instrument 355 (e.g., one of the instruments used to obtain the biomedical image data described above), which may be coupled to an instrument computer 351. Each computer in the system 300 includes a processor 337 coupled to a tangible, non-transitory memory device 375 and at least one input/output device 335. Thus, the system 300 includes at least one processor 337 coupled to a memory subsystem 375 (e.g., a memory device or collection of memory devices). The components (e.g., computer, server, instrument computer, and imaging instrument) may be in communication over a network 315 that may be wired or wireless and wherein the components may be remotely located or located in close proximity to each other. Using those components, the system 300 is operable to receive or obtain training data such as tissue images and outcome data as well as test sample images generated by the imaging instrument or otherwise obtained. In certain embodiments, the system uses the memory to store the received data as well as the model data which may be trained and otherwise operated by the processor.

In some embodiments, some or all of system 300 is implemented in a cloud-based architecture. The cloud-based architecture may offer on-demand access to a shared pool of configurable computing resources (e.g., processors, graphics processors, memory, disk storage, network bandwidth, and other suitable resources). A processor in the cloud-based architecture may be operable to receive or obtain training data such as tissue images and outcome data as well as test sample images generated by the imaging instrument or otherwise obtained. A memory in the cloud-based architecture may store the received data as well as the model data which may be trained and otherwise operated by the processor. In some embodiments, the cloud-based architecture may provide a graphics processor for training the model in a faster and more efficient manner compared to a conventional processor.

Processor refers to any device or system of devices that performs processing operations. A processor will generally include a chip, such as a single core or multi-core chip (e.g., 12 cores), to provide a central processing unit (CPU). In certain embodiments, a processor may be a graphics processing unit (GPU) such as an NVidia Tesla K80 graphics card from NVIDIA Corporation (Santa Clara, Calif.). A processor may be provided by a chip from Intel or AMD. A processor may be any suitable processor such as the microprocessor sold under the trademark XEON E5-2620 v3 by Intel (Santa Clara, Calif.) or the microprocessor sold under the trademark OPTERON 6200 by AMD (Sunnyvale, Calif.). Computer systems may include multiple processors including CPUs and or GPUs that may perform different steps of the described methods. The memory subsystem 375 may contain one or any combination of memory devices. A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Each computer may include a non-transitory memory device such as a solid state drive, flash drive, disk drive, hard drive, subscriber identity module (SIM) card, secure digital card (SD card), micro SD card, or solid state drive (SSD), optical and magnetic media, others, or a combination thereof. Using the described components, the system 300 is operable to produce a report and provide the report to a user via an input/output device. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

References and citations to other documents, such as patents, patent applications, patent publications, journals, books, papers, web contents, have been made throughout this disclosure and in any patent applications incorporated by reference herein. All such documents are hereby incorporated herein by reference in their entirety for all purposes.

The invention claimed is:

1. A method for classifying biomedical image data, the method comprising:
    generating, by at least one computer processor, an annotated representation of biomedical image data;
    identifying, by the at least one computer processor, a plurality of pixel clusters based on the biomedical image data;
    constructing, by the at least one computer processor, a graph based on the plurality of pixel clusters;
    determining, by the at least one computer processor, at least one biomedical feature for at least one node of the graph based on the annotated representation of the biomedical image data; and
    processing, by the at least one computer processor, a graph neural network to classify the biomedical image data based on the at least one biomedical feature, wherein the graph neural network includes at least one layer that transforms an input graph with at least one node feature into an updated graph, wherein the at least one node feature is updated in the updated graph.

2. The method of claim 1, wherein the method further comprises classifying the biomedical image data by predicting a severity of a disease condition.

3. The method of claim 1, wherein the biomedical image data comprises a hematoxylin and eosin (H&E) stained whole slide image, and wherein the method further comprises classifying the biomedical image data by predicting a non-alcoholic fatty liver disease activity score (NAS) based on the H&E stained whole slide image.

4. The method of claim 1, wherein the biomedical image data comprises a trichrome-stained whole slide image, and wherein the method further comprises classifying the biomedical image data by predicting a Clinical Research Network (CRN) score based on the trichrome-stained whole slide image.

5. The method of claim 1, wherein the graph neural network comprises at least one graph convolution module and at least one graph pooling module, and wherein the at least one graph pooling module uses at least one of edge pooling or self-attention pooling.

6. The method of claim 1, further comprising training, based on labeled training data, the graph neural network using a mixed effects model, wherein the training comprises:
   learning one or more bias parameters associated with each individual that assigned a label to the labeled training data; and
   adjusting a prediction of the graph neural network based on the one or more bias parameters when training using the labeled training data labeled by the corresponding individual.

7. The method of claim 1, wherein the at least one biomedical feature comprises an aggregate metric based on at least one second biomedical feature identified in the annotated representation of the biomedical image data, wherein the aggregate metric comprises at least one of a mean, a standard deviation, a skewness, a kurtosis, or an entropy of the at least one second biomedical feature associated with each pixel cluster among the plurality of pixel clusters.

8. The method of claim 1, wherein identifying the plurality of pixel clusters comprises:
   randomly sampling a plurality of pixels from the biomedical image data;
   processing the randomly sampled plurality of pixels into the plurality of pixel clusters; and
   assigning a remaining plurality of pixels from the biomedical image data to a corresponding pixel cluster among the plurality of pixel clusters based on a nearest neighbor among the randomly sampled plurality of pixels.

9. The method of claim 1, wherein generating the annotated representation comprises processing the biomedical image data using one or more convolutional neural network models, wherein the annotated representation is based on logit values generated by the one or more convolutional neural network models.

10. A system for classifying biomedical image data comprising:
   at least one computer processor, wherein the at least one computer processor is configured to:
      generate an annotated representation of biomedical image data;
      identify a plurality of pixel clusters based on the biomedical image data;
      construct a graph based on the plurality of pixel clusters;
      determine at least one biomedical feature for at least one node of the graph based on the annotated representation of the biomedical image data; and
      process a graph neural network to classify the biomedical image data based on the at least one biomedical feature, wherein the graph neural network includes at least one layer that transforms an input graph with at least one node feature into an updated graph, wherein the at least one node feature is updated in the updated graph.

11. The system of claim 10, wherein the at least one computer processor is further configured to classify the biomedical image data by predicting a severity of a disease condition.

12. The system of claim 10, wherein the biomedical image data comprises a hematoxylin and eosin (H&E) stained whole slide image, and wherein the at least one computer processor is further configured to classify the biomedical image data by predicting a non-alcoholic fatty liver disease activity score (NAS) based on the H&E stained whole slide image.

13. The system of claim 10, wherein the biomedical image data comprises a trichrome-stained whole slide image, and wherein the at least one computer processor is further configured to classify the biomedical image data by predicting a Clinical Research Network (CRN) score based on the trichrome-stained whole slide image.

14. The system of claim 10, wherein the graph neural network comprises at least one graph convolution module and at least one graph pooling module, and wherein the at least one graph pooling module uses at least one of edge pooling or self-attention pooling.

15. The system of claim 10, wherein the at least one computer processor is further configured to train, based on labeled training data, the graph neural network using a mixed effects model, wherein the training comprises:
   learning one or more bias parameters associated with each individual that assigned a label to the labeled training data; and
   adjusting a prediction of the graph neural network based on the one or more bias parameters when training using the labeled training data labeled by the corresponding individual.

16. The system of claim 10, wherein the at least one biomedical feature comprises an aggregate metric based on at least one second biomedical feature identified in the annotated representation of the biomedical image data, wherein the aggregate metric comprises at least one of a mean, a standard deviation, a skewness, a kurtosis, or an entropy of the at least one second biomedical feature associated with each pixel cluster among the plurality of pixel clusters.

17. The system of claim 10, wherein identifying the plurality of pixel clusters comprises:
   randomly sampling a plurality of pixels from the biomedical image data;
   processing the randomly sampled plurality of pixels into the plurality of pixel clusters; and
   assigning a remaining plurality of pixels from the biomedical image data to a corresponding pixel cluster among the plurality of pixel clusters based on a nearest neighbor among the randomly sampled plurality of pixels.

18. The system of claim 10, wherein generating the annotated representation comprises processing the biomedical image data using one or more convolutional neural network models, wherein the annotated representation is based on logit values generated by the one or more convolutional neural network models.

19. An article of manufacture for classifying biomedical image data comprising:
a non-transitory processor readable medium; and
instructions stored on the medium;
wherein the instructions are configured to be readable from the medium by at least one computer processor and thereby cause the at least one computer processor to operate so as to:
generate an annotated representation of biomedical image data;
identify a plurality of pixel clusters based on the biomedical image data;
construct a graph based on the plurality of pixel clusters;
determine at least one biomedical feature for at least one node of the graph based on the annotated representation of the biomedical image data; and
process a graph neural network to classify the biomedical image data based on the at least one biomedical feature, wherein the graph neural network includes at least one layer that transforms an input graph with at least one node feature into an updated graph, wherein the at least one node feature is updated in the updated graph.

20. The article of manufacture of claim 19, wherein the at least one computer processor is further caused to operate so as to classify the biomedical image data by predicting a severity of a disease condition.

21. The article of manufacture of claim 19, wherein the biomedical image data comprises a hematoxylin and eosin (H&E) stained whole slide image, and wherein the at least one computer processor is further caused to operate so as to classify the biomedical image data by predicting a non-alcoholic fatty liver disease activity score (NAS) based on the H&E stained whole slide image.

22. The article of manufacture of claim 19, wherein the biomedical image data comprises a trichrome-stained whole slide image, and wherein the at least one computer processor is further caused to operate so as to classify the biomedical image data by predicting a Clinical Research Network (CRN) score based on the trichrome-stained whole slide image.

23. The article of manufacture of claim 19, wherein the graph neural network comprises at least one graph convolution module and at least one graph pooling module, and wherein the at least one graph pooling module uses at least one of edge pooling or self-attention pooling.

24. The article of manufacture of claim 19, wherein the at least one computer processor is further configured to operate so as to train, based on labeled training data, the graph neural network using a mixed effects model, wherein the training comprises:
learning one or more bias parameters associated with each individual that assigned a label to the labeled training data; and
adjusting a prediction of the graph neural network based on the one or more bias parameters when training using the labeled training data labeled by the corresponding individual.

25. The article of manufacture of claim 19, wherein the at least one biomedical feature comprises an aggregate metric based on at least one second biomedical feature identified in the annotated representation of the biomedical image data, wherein the aggregate metric comprises at least one of a mean, a standard deviation, a skewness, a kurtosis, or an entropy of the at least one second biomedical feature associated with each pixel cluster among the plurality of pixel clusters.

26. The article of manufacture of claim 19, wherein identifying the plurality of pixel clusters comprises:
randomly sampling a plurality of pixels from the biomedical image data;
processing the randomly sampled plurality of pixels into the plurality of pixel clusters; and
assigning a remaining plurality of pixels from the biomedical image data to a corresponding pixel cluster among the plurality of pixel clusters based on a nearest neighbor among the randomly sampled plurality of pixels.

27. The article of manufacture of claim 19, wherein generating the annotated representation comprises processing the biomedical image data using one or more convolutional neural network models, wherein the annotated representation is based on logit values generated by the one or more convolutional neural network models.

* * * * *